United States Patent [19]
Bodart

[11] Patent Number: 5,432,243
[45] Date of Patent: Jul. 11, 1995

[54] PROCESS FOR THE POLYMERIZATION OF OLEFINS

[75] Inventor: Philippe Bodart, Engis, Belgium

[73] Assignee: Fina Research, S.A., Feluy, Belgium

[21] Appl. No.: 305,318

[22] Filed: Sep. 15, 1994

[30] Foreign Application Priority Data

Sep. 15, 1993 [EP] European Pat. Off. ............ 93870188

[51] Int. Cl.$^6$ .................................................. C08F 2/14
[52] U.S. Cl. ........................................ 526/68; 526/351; 528/482
[58] Field of Search ................... 526/68, 351, 482

[56] References Cited

U.S. PATENT DOCUMENTS

| | | | |
|---|---|---|---|
| 4,861,939 | 8/1989 | Debras et al. | 585/820 |
| 5,134,208 | 7/1992 | Burstain | 526/68 |

Primary Examiner—Joseph L. Schofer
Assistant Examiner—Tom Weber
Attorney, Agent, or Firm—M. Norwood Cheairs; Jim D. Wheelington

[57] ABSTRACT

Olefin polymerization is conducted with a Ziegler-Natta catalyst in which unreacted monomer is recycled to the reactor. The recycle line contains a supported nickel or nickel oxide to purify the unreacted monomer before its return to the reactor, and results in improved catalyst activity and more control over physical properties of the product.

3 Claims, 4 Drawing Sheets

PROCESS FOR THE POLYMERIZATION OF OLEFINS

TECHNICAL FIELD OF THE INVENTION

The present invention relates to an improved process for the polymerization of olefins. More particularly, the present invention relates to a process for the polymerization of olefins by high yield catalysts of the Ziegler-Natta type, whereby a better control over specifications of the product and/or a better yield is obtained.

BACKGROUND OF THE INVENTION

Industrial applications of light olefin-containing hydrocarbons, and particularly liquified propylene, have become more increasingly specialized. The technology as presently developed utilizes highly efficient catalysts to convert these light olefins into final products such as polymers, any excess being recycled. The latest technology in propylene polymerization uses as solvent the propylene itself, the large excess of which is recycled. Since these highly efficient catalysts are very sensitive, impurities in recycled olefins may deactivate them at least partially, leading to a productivity decrease. Further, some impurities may gradually accumulate in the recycle stream. It has also been observed that some properties and particularly the melt flow index of the polymers is unstable as a function of time.

As a result, there is a real need to improve techniques for the polymerization of olefins, more particularly when high yield catalysts are used.

SUMMARY OF THE INVENTION

It is an object of the invention to provide an improved process for the polymerization of olefins.

Another object of this invention is to provide a process comprising a recycle of the monomer whereby polymer/catalyst ratios are increased.

Still another object of the invention is to provide a process comprising a recycle of the monomer whereby a better control of specifications of the polymer is obtained.

In accordance with the present invention, the process of the invention comprises at least the steps of:
(i) converting part of the light olefins contained in a hydrocarbon feedstock into a polymer over a Ziegler-Natta type catalyst;
(ii) separating the polymer from the unreacted feedstock;
(iii) passing the said unreacted feedstock over a material comprising nickel deposited on a support material and wherein the nickel is present in the forms of metallic nickel and of nickel oxide;
(iv) recycling the feedstock into step (i).

Light olefins, as used herein, are $C_2$-$C_6$ olefins. Of particular interest are ethylene and propylene, with 1-hexene sometimes being used for the preparation of copolymers with ethylene.

The hydrocarbon feedstocks may contain substantially pure olefins, mixtures thereof, or mixtures of olefins with saturated hydrocarbons, like hexane or cyclohexane. In polypropylene production, the hydrocarbon feedstock generally comprises more than 75 wt. % propylene, more particularly from 85 to 90 wt. % propylene. In polyethylene production, the hydrocarbon feedstock generally comprises more than 80 wt. % of ethylene, more particularly from 90 to 99 wt. %.

The improvement provided by this invention may be used in combination with any polymerization process using a Ziegler-Natta type catalyst. Such processes and catalysts are well-known in the art and need not be described further.

After the polymerization reaction, the polymer thus formed is separated from the remainder of the olefins and of any saturated hydrocarbons present, usually by flashing.

In a further step, what remains of the feedstock is passed over a material before recycling. The material used comprises nickel deposited on a support material, the nickel being present both as metallic nickel and as nickel oxide. Silicas, silica-aluminas, aluminas, kieselguhr, zeolites and other similar materials, whether amorphous or crystalline, can be utilized as the support, provided sufficient metal dispersion is obtained.

The total weight of nickel and nickel oxide may represent from 10 wt. % up to about 80 wt. % of the material. Accordingly, the material may include 20 to 90 wt. % of the support. Preferably, the weight ratio of metallic nickel to nickel oxide is of 0.4 to 2.0, with the provision that metallic nickel should neither represent less than 6 wt. % nor more than 50 wt. % of the material, and the material comprises from 40 to 70 wt. % of nickel (total weight Ni+NiO) and from 30 to 60 wt. % of support. When carrying out the process of the invention with a material outside this definition, the results obtained are less satisfactory. While the invention is not to be limited by any theory, it is believed that larger crystallites are formed if the Ni/NiO ratio is higher than 2.0, thus leading to a lesser efficiency; similarly, an excessive total nickel content tends to lower the specific surface and consequently the efficiency, while a too low total nickel content would lead to an insufficient capacity.

The nickel can be deposited on the support by any suitable technique. Several methods are well known to those skilled in the art. For example, nickel can be deposited on the support by dissolving nickel nitrate in water, mixing the solution with the support and precipitating the nickel, for example in the form of nickel carbonate, and subsequently washing, drying and calcining the precipitate. The nickel deposited in this manner is then partially reduced by means of hydrogen to form metallic nickel, the remainder being in the form of nickel oxide.

In general, the size of the nickel crystallites after reduction is from about 1 to about 20 nanometers (nm). A more specific size range is about 1–2 nm. The size of the nickel crystallites depends on the extent of reduction carried out. In fact, if the degree of reduction is increased, the size of the crystallites increases to above the aforementioned range and the material obtained does not have the preferred properties. On the other hand, if the degree of reduction is too low, the crystallites still have good dimensions but the quantity of nickel available in this case is too small to ensure successful purification of the feedstock.

The specific surface area of the material obtained after reduction is generally higher than 100 $m^2$/g.

The particle size of the material depends especially on the pressure drop allowed in the reactor. The material is generally used under the form of powder, pellets, extrudates or spheres. Preferably, the particle diameter of this material when spherical does not exceed about 3.5 mm and is most preferably from 1 to 2.5 mm; when cylindrical particles are used, they preferably have a diameter of from 1 to 4 mm and a length form 3 to 8 mm. When using extrudates, they should preferably be trilobes in order to increase the external surface of the particles, thus favoring absorption.

In one embodiment of the present invention, propylene feedstock is passed over the material at a temperature of from −10° C. to 90° C., preferably of from 10° C. to 40° C., and under sufficient pressure to keep the medium in the liquid phase. The weight hourly space velocity (WHSV) utilized is from 0.1 to 25 and preferably from 1 to 10.

In another embodiment, ethylene feedstock is passed over the material at a temperature of from −10° C. to 80° C., preferably from 10° C. to 40° C., under a pressure of at least 1 MPa (10 bars), and with a WHSV of from 0.1 to 25, preferably of from 1 to 10.

It is surprising that the material used in the process of the invention would have any efficiency after the polymerization reaction. Indeed, that material is known from Belgian Patent No. 902942 to remove COS from liquid olefinic feedstock, and from European Patent No. 308569 to remove arsine form the same feedstocks. COS and arsine are known to be able to react even in traces with the polymerization catalysts, so that the feedstock recovered after the polymerization no longer contains any COS or arsine and would be expected by one skilled in the art to be recyclable without any treatment.

DETAILED DESCRIPTION

Figure 1:
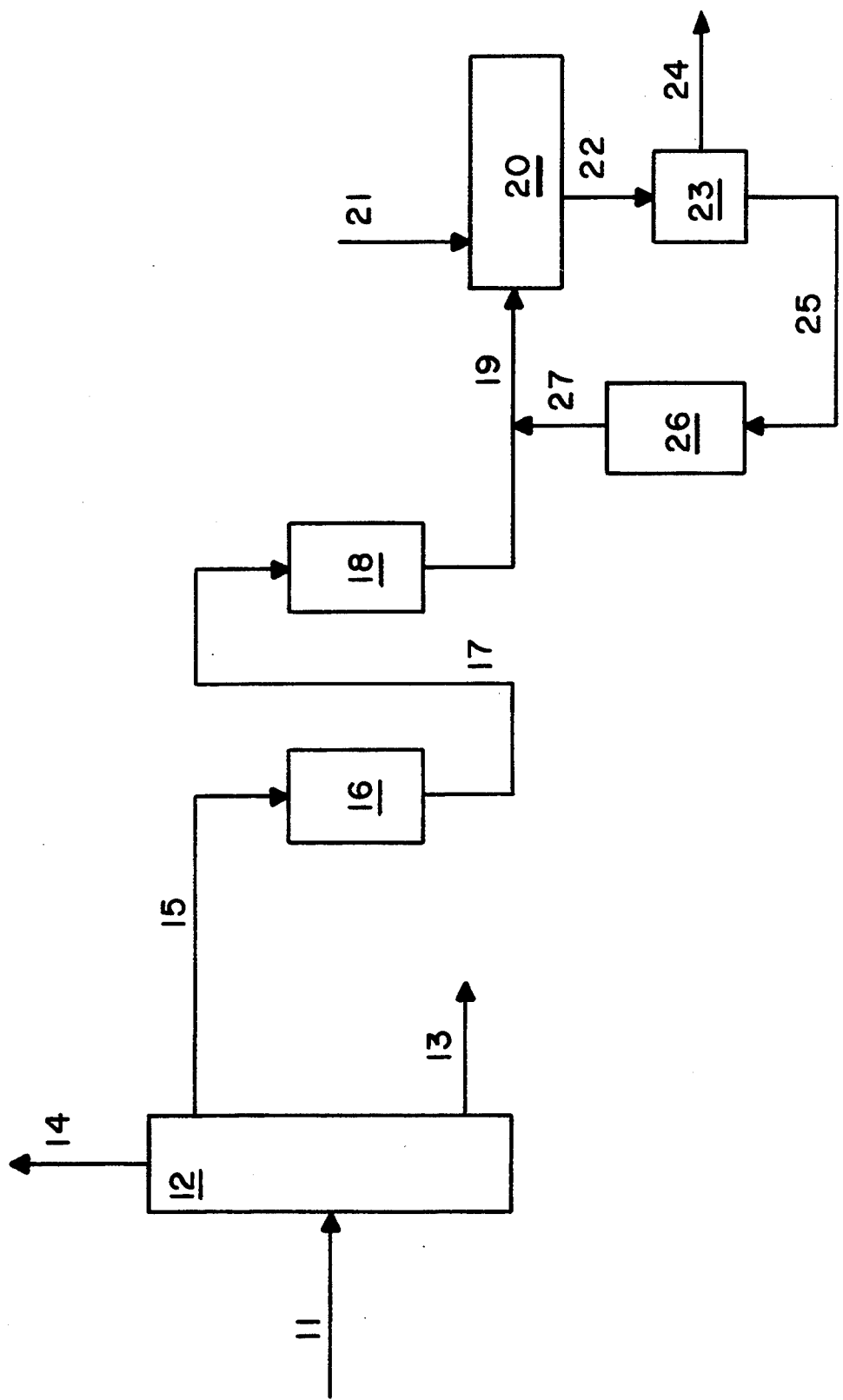
FIG. 1 illustrates an embodiment in which an olefinic feedstock to be recycled is passed over the material before combining it with the fresh feedstock.

The invention will now be described in greater detail below with reference to the accompanying drawings in which:

Referring now to FIG. 1, a fresh olefinic feed is fed through line 11 into a distillation column 12. The heavier fraction, essentially comprising the corresponding alkane, is recovered through pipe 13, while the lighter fraction exits through pipe 14. The olefinic fraction is passed via pipe 15 into a dryer 16, then via pipe 17 through a purification unit 18 which contains absorbent material for COS and arsine that may or may not be the same or of the same type as that required by this invention. The feedstock thus purified is sent via pipe 19 to the polymerization unit 20, in which the other ingredients (catalyst, cocatalyst, stereoregulator, hydrogen, and others, as required by the polymerization process) are fed through pipe 21. The mixture of polymer, unreacted monomer(s) and possible alkane(s) is then sent via pipe 22 to a flashing unit 23 to separate the polymer (24) from the hydrocarbons removed through pipe 25. Said hydrocarbon feedstock is then passed through a reactor 26 containing a supported Ni/NiO material according to this invention, then recycled into pipe 19 via pipe 27.

Figure 2:
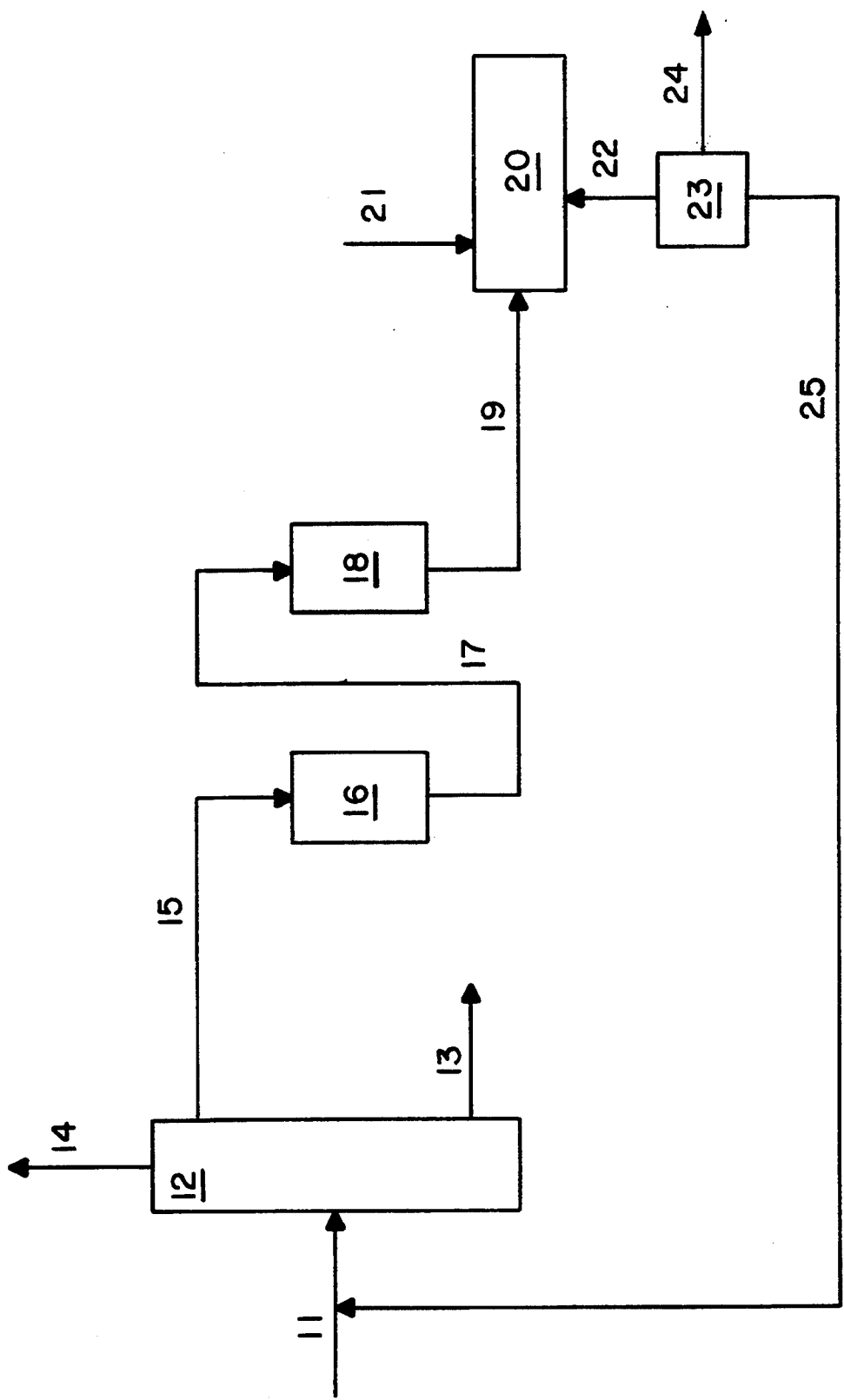
FIGS. 2 to 4 illustrate embodiments in which the feedstock to be recycled is combined with the fresh feedstock before passing them together over the same material.
Figure 3:
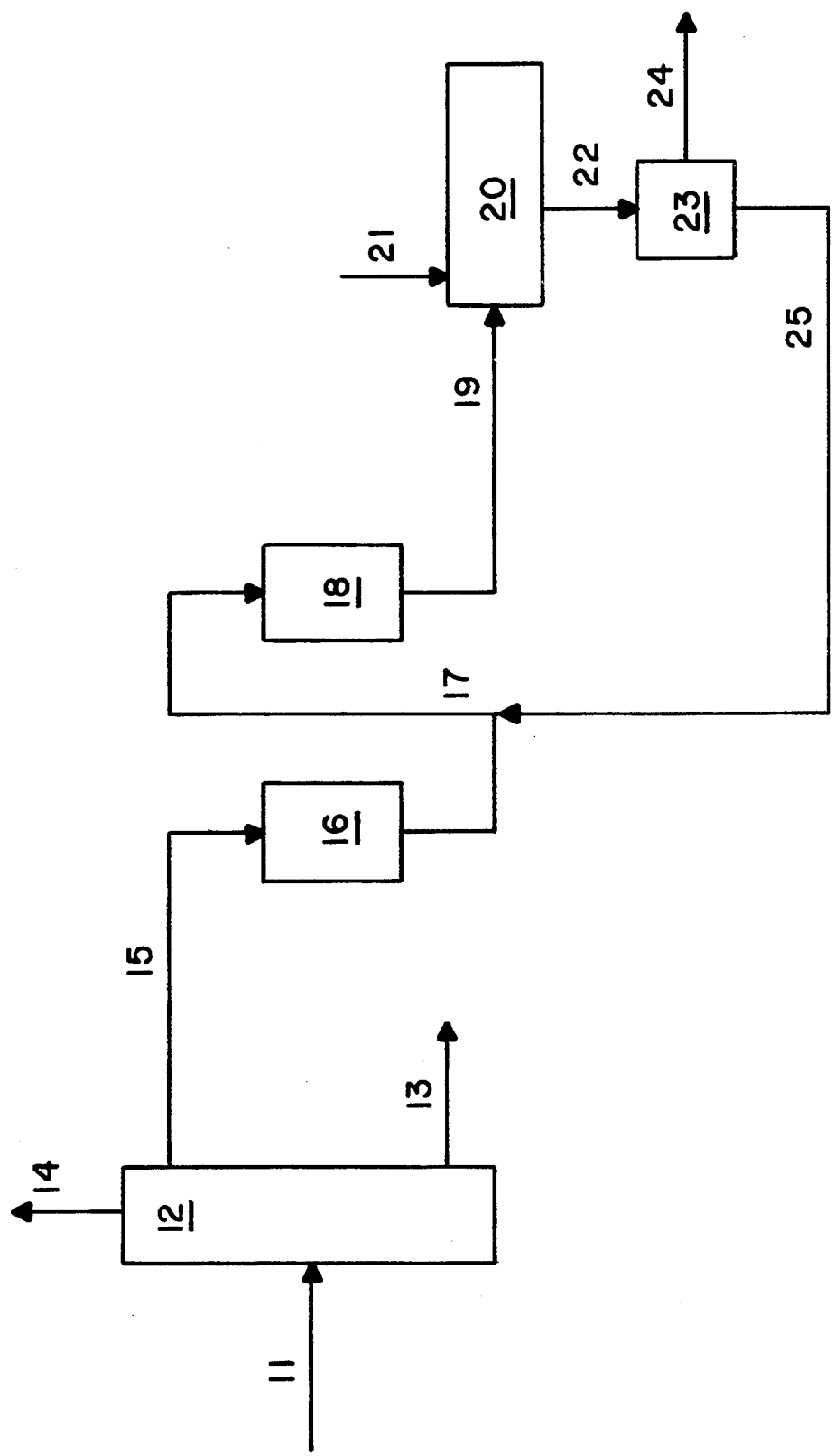
Figure 4:
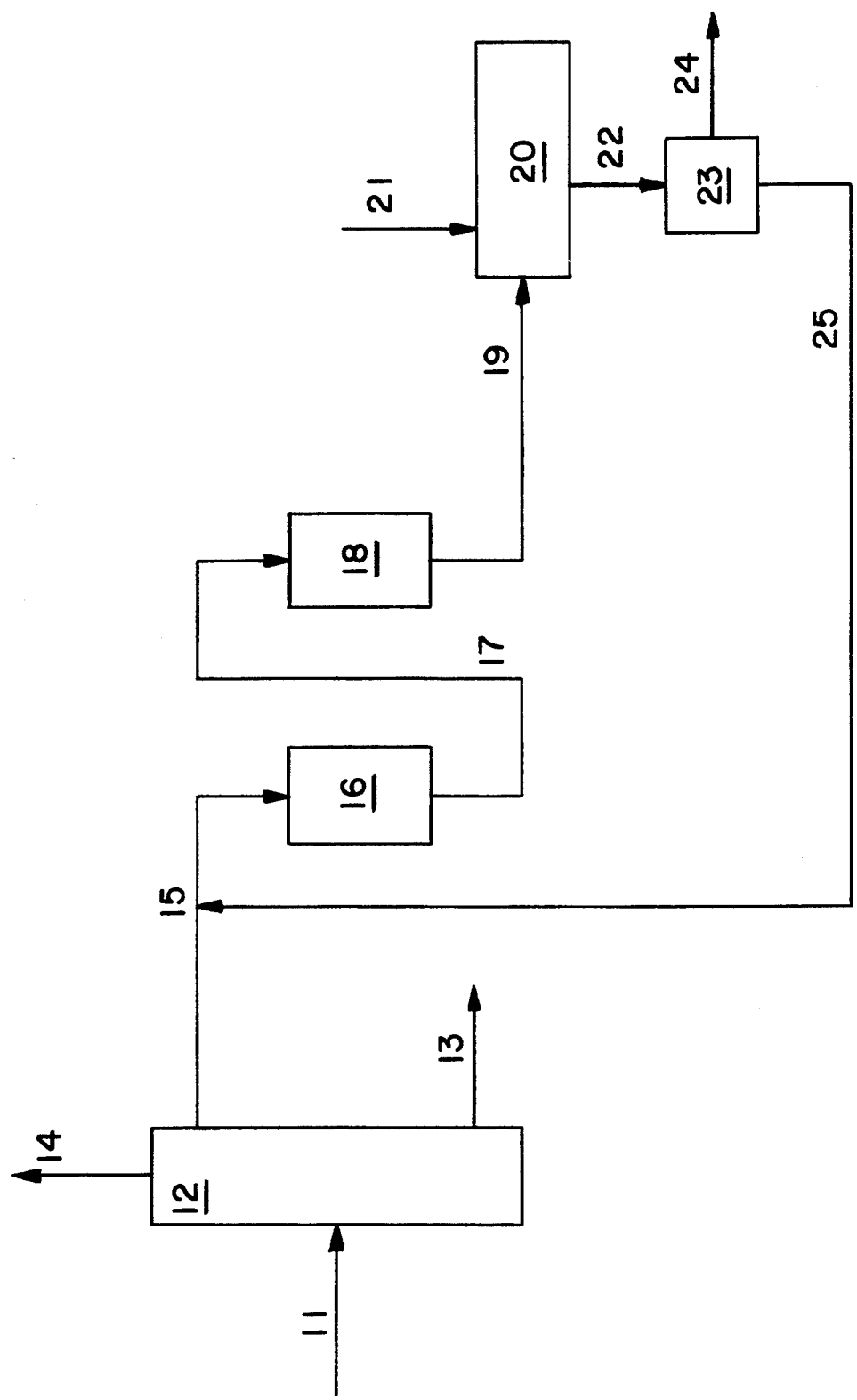

FIGS. 2 and 3 describe embodiments in which the hydrocarbon feedstock recovered from the flashing unit 23 is fed through pipe 25 for recycling into pipe 11 (FIG. 2), pipe 17 (FIG. 3) or pipe 15 (FIG. 4), the absorbent material in unit 18 being of the type required by this invention.

Although specific embodiments of the present invention have been described in the detailed description above, the description is not intended to limit the invention to the particular forms or embodiments disclosed therein, since they are to be recognized as illustrative rather than restrictive and it will be obvious to one skilled in the art that the invention is not so limited.

For example, the recovered hydrocarbon feedstock, whether treated separately or not, can be recycled in other appropriate parts of the polymerization unit. Further, depending on the purity of the fresh feedstock, the polymerization unit may comprise less or more purification units. Other configurations or components of the polymerization unit may be envisaged.

The example which follows is given in order to provide a better illustration of the process of the present invention, but without thereby restricting its scope.

EXAMPLE

Liquid propylene was fed into a pilot polymerization unit having a configuration as shown in FIG. 3.

The absorbent material in unit 18 was silica-alumina as the support (representing 43.3 wt. % of the material) on which nickel was deposited, the nickel being present in the form of NiO and metallic Ni, the weight ratio Ni/NiO being of 0.668. The absorbent material was under the form of cylindrical extrudates of about 1 mm diameter and 3 mm length. The specific surface area of that material was of 145 $m_2$/g. The size of the nickel crystallites was of about 2 nm.

The liquid propylene feedstock had the following composition and impurities in pipe 11:

| propylene | 96.5 wt. % |
| --- | --- |
| propane | 3.1 wt. % |
| C4 hydrocarbons | 0.4 wt. % |
| water | 30 ppm |
| COS | 10 ppb |
| arsine | 75 ppb |

After passage through unit 18 (at a temperature of 20° C., under a pressure of 1.5 MPa (15 bars) and a WHSV of 6 kg/kg.h), the feedstock had a COS content lower than 5 ppb (detection limit) and an arsine content lower than 3 ppb (detection limit).

Continuous polymerization was carried out in unit 20, using a Ziegler-Natta type catalyst fed through pipe 21 with the other usual ingredients required by the polymerization process. The average yield was of 13200 g of polypropylene per g of catalyst (standard deviation 100 g/g). The melt flow index was stable to less than 1%.

COMPARATIVE EXAMPLE

Example 1 was repeated with the difference that pipe 25 was connected to pipe 19, hence the recycled feedstock was no longer passing through unit 18. The average yield was of 11800 g/g (standard deviation 150 g/g). The melt flow index was unstable, showing extreme variations of about 8% over one day under constant experimental conditions.

I claim:

1. A process for the polymerization of olefins comprising at least the steps of:
   (i) converting part of the light olefins contained in a hydrocarbon feedstock into a polymer over a Ziegler-Natta type catalyst;
   (ii) separating the polymer from the unreacted feedstock;

(iii) passing the said unreacted feedstock over a material comprising nickel deposited on a support material and wherein the nickel is present in the forms of metallic nickel and of nickel oxide;

(iv) recycling the feedstock into step (i).

2. In a process for the polymerization of olefins over a Ziegler-Natta type catalyst with recycling of the unreacted olefins, the improvement which consists of passing the recycled olefins over a material comprising nickel deposited on a support material, the nickel being present in the forms of metallic nickel and nickel oxide.

3. Process according to either of claims 1 or 2, wherein the weight ratio of metallic nickel to nickel oxide is of 0.4 to 2.0, with the provision that metallic nickel should neither represent less than 6 wt. % nor more than 50 wt. % of the material, and the material comprises from 40 to 70 wt. % of nickel (total weight Ni+NiO) and from 30 to 60 wt. % of support.

* * * * *